US00PP31905P2

(12) United States Plant Patent
Hughes

(10) Patent No.: US PP31,905 P2
(45) Date of Patent: Jun. 23, 2020

(54) ***PELARGONIUM* PLANT NAMED 'HUGHES GOLD'**

(50) Latin Name: ***Pelargonium* x *hortorum***
Varietal Denomination: Hughes Gold

(71) Applicant: Jared Edward Hughes, Marengo, OH (US)

(72) Inventor: Jared Edward Hughes, Marengo, OH (US)

( * ) Notice: Subject to any disclaimer, the term of this patent is extended or adjusted under 35 U.S.C. 154(b) by 0 days.

(21) Appl. No.: 16/602,302

(22) Filed: Sep. 6, 2019

(51) Int. Cl.
*A01H 5/02* (2018.01)
*A01H 6/42* (2018.01)

(52) U.S. Cl.
USPC ..... Plt./325

(58) Field of Classification Search
USPC ..... Plt./325
CPC ..... A01H 5/02; A01H 6/42
See application file for complete search history.

*Primary Examiner* — Annette H Para
(74) *Attorney, Agent, or Firm* — Penny J. Aguirre

(57) ABSTRACT

A new cultivar of *Pelargonium* plant named 'Hughes Gold' that is characterized by its foliage with bright gold/chartreuse new growth and changes to chartreuse as it matures, its solid orange colored flowers, and its well branched plant habit and good vigor.

2 Drawing Sheets

Botanical classification: *Pelargonium* x *hortorum.*
Cultivar designation: 'Hughes Gold'.

BACKGROUND OF THE INVENTION

The present invention relates to a new and distinct cultivar of *Pelargonium* plant, botanically known as *Pelargonium* x *hortorum* 'Hughes Gold' and will be referred to hereafter by its cultivar name, 'Hughes Gold'. 'Hughes Gold' represents a new cultivar of zonal geranium grown as an ornamental annual for container use.

The new cultivar was discovered by the Inventor in March of 2018 as a naturally occurring branch mutation of the *Pelargonium* x *hortorum* cultivar 'Crystal Palace Gem' (not patented) that was growing in a container in a greenhouse in Marengo, Ohio.

Asexual reproduction of the new cultivar was first accomplished by stem cuttings in in March of 2018 by the Inventor in Marengo, Ohio. Asexual reproduction by stem cuttings has determined that the characteristics of this cultivar are stable and are reproduced true to type in successive generations.

SUMMARY OF THE INVENTION

The following traits have been repeatedly observed and represent the characteristics of 'Hughes Gold'. These attributes in combination distinguish 'Hughes Gold' as a new and distinct cultivar of *Pelargonium.*

1. 'Hughes Gold' exhibits foliage with bright gold/chartreuse new growth and changes to chartreuse as it matures.
2. 'Hughes Gold' exhibits solid orange colored flowers.
3. 'Hughes Gold' exhibits a well branched plant habit and good vigor.

The parent of 'Hughes Gold', 'Crystal Palace Gem', differs from 'Hughes Gold' in having chartruese colored foliage with a prominent green area on the centers of the leaves. The new cultivar, 'Hughes Gold', can be most closely compared to *Pelargonium* cultivars 'Persian Queen' (not patented) and 'Wilhelm Langguth' (not patented). 'Persian Queen' is similar to 'Hughes Gold' in having gold foliage and inflorescences that are similar in size. 'Persian Queen' differs from 'Hughes Gold' in having flowers that are fuschia pink in color. 'Wilhelm Langguth' is similar to 'Hughes Gold' in plant size and vigor. 'Wilhelm Langguth' differs from 'Hughes Gold' in having leaves that are variegated with green centers and white margins and flowers that are true red in color.

BRIEF DESCRIPTION OF THE DRAWINGS

The accompanying colored photographs illustrate the overall appearance and distinct characteristics of the new *Pelargonium*. The following is a detailed description of a 5 month-old plants as grown in a greenhouse in a 8.5-inch container in Marengo, Ohio.

The photograph in FIG. 1 is a view of a plant of 'Hughes Gold' in bloom.

Figure 1:
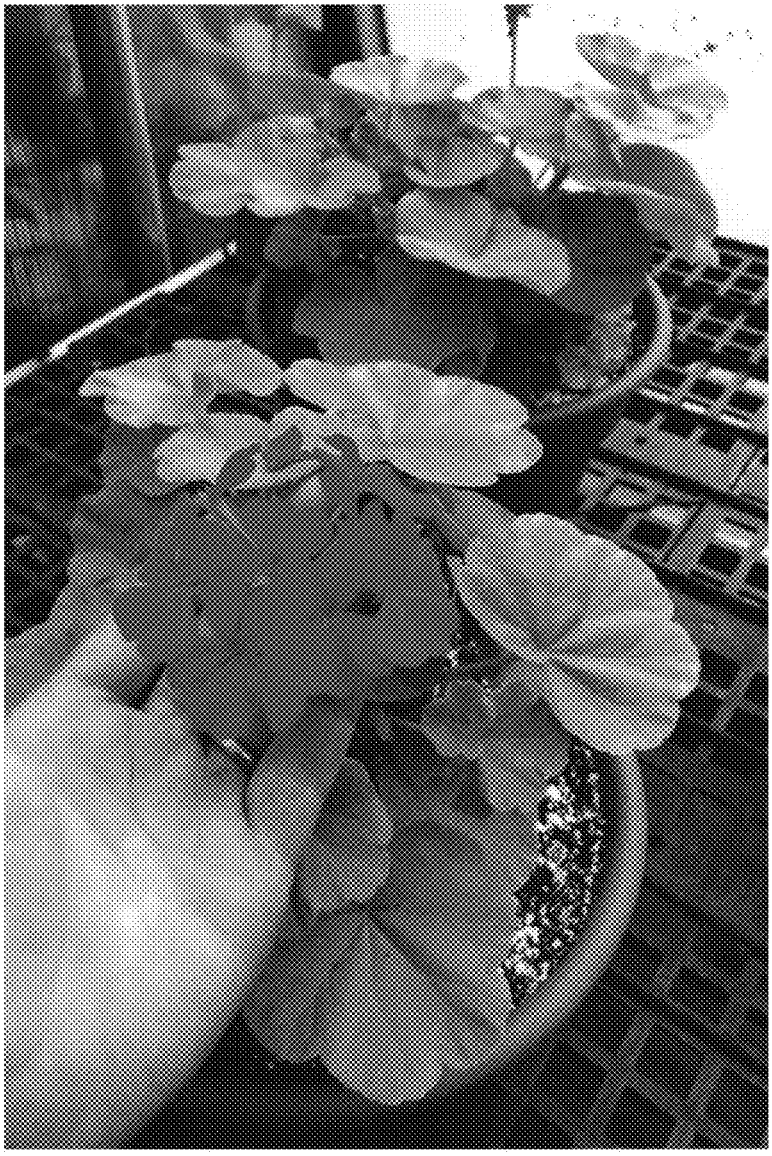
Figure 2:
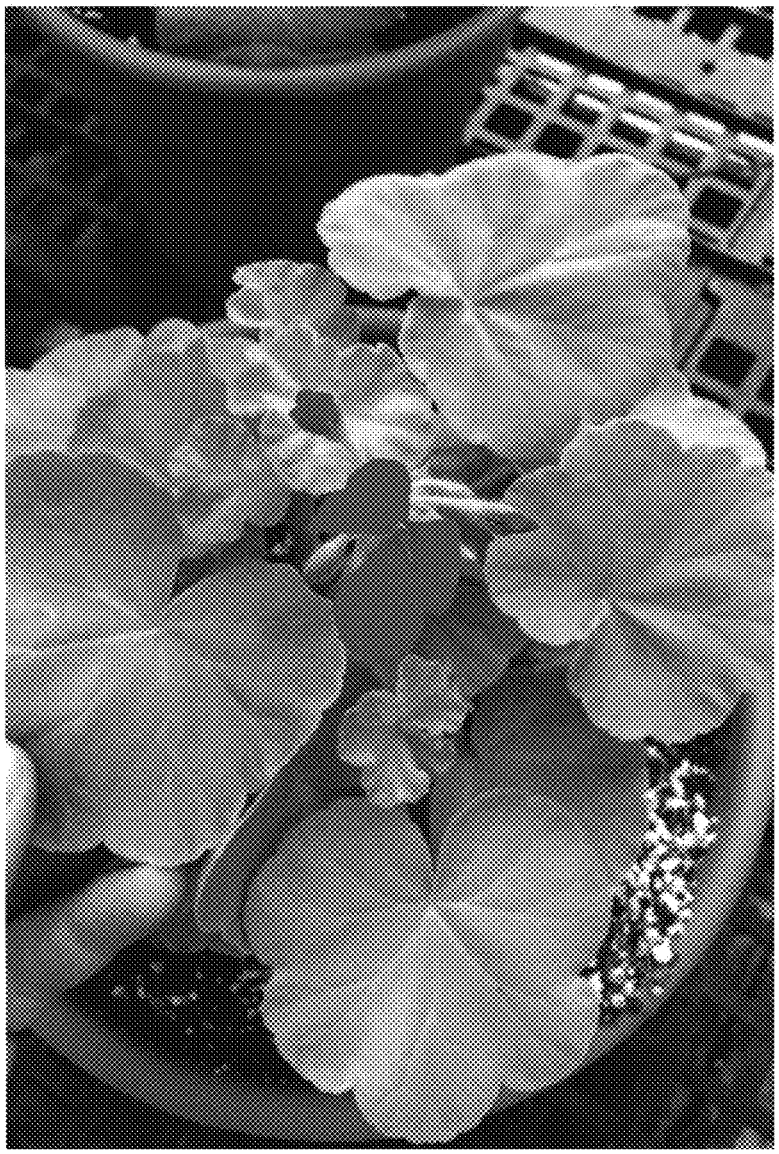

The photograph in FIG. 2 is of a view of a newly opening flower of 'Hughes Gold'.

The colors in the photographs are as close as possible with the photographic and printing technology utilized and the color values cited in the detailed botanical description accurately describe the colors of the new *Pelargonium.*

DETAILED BOTANICAL DESCRIPTION OF THE PLANT

The following is a detailed description of 10-weeks old plants as grown outdoors in 8.5-inch containers in in Marengo, Ohio. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General characteristics:

*Blooming period*.—Continuously throughout the growing season.

*Plant type*.—Blooming annual.

*Plant habit*.—Upright and mounding.

*Height and spread*.—Reaches about 61 cm in height and spread as a 3-month-old plant in a container.

*Cold hardiness*.—At least to U.S.D.A. Zones 9 to 11, grown as a annual.

*Diseases and pests*.—No susceptibility or resistance to pests or diseases has been observed.

*Root description*.—Fibrous, 164C in color.

*Branching habit*.—Well-branched.

*Growth rate*.—Moderately vigorous.

*Propagation*.—Stem cuttings.

*Root development*.—Roots initiate in 12 to 14 days, a young rooted plant is produced in 4 to 5 weeks.

Stem description:

*Stem size*.—Main stem; 3 cm in length and 9 mm in width, lateral stems (2); an average of 27.5 cm in length and 7 mm in width.

*Stem shape*.—Round-oval.

*Stem strength*.—Moderately strong.

*Stem color*.—144C with leaf nodes 149D.

*Stem surface*.—Matt and slightly glandular.

*Internode length*.—Average of 7 mm.

Foliage description:

*Leaf shape*.—Orbicular.

*Leaf division*.—Single.

*Leaf base*.—Cordate.

*Leaf apex*.—Rounded.

*Leaf venation*.—Palmate, 141D on upper and lower surfaces.

*Leaf margins*.—Palmate shallow lobes; average of 5, lobe margins crenate.

*Leaf attachment*.—Petiolate.

*Leaf arrangement*.—Opposite to subopposite.

*Leaf surface*.—Upper surface matt and very finely pubescent, lower surface matt, glabrous with veins finely pubescent.

*Leaf color*.—Young and unshaded upper surface; 150B and N144B, young and unshaded lower surface; blend of 144C and N144D, mature and shaded upper surface; a color between 144A and 138A with center blotches of 144C, mature and shaded lower surface; 138B with some mottling of 144D.

*Leaf size*.—Matures to an average of 6.5 cm in length and 7.3 cm in diameter.

*Leaf quantity*.—Average of 10 per lateral branch (with some lower leaves dropped).

*Petioles*.—An average of 6 cm in length and 2.5 mm in diameter, 144D in color, very finely pubescent surface.

*Stipules*.—Leafy stipule present at the base of petiole; lanceolate to ovate in shape, apex cuspidate, margin entire, base truncate, average of 1 cm in length and 7 mm in width, 144D in color on both surfaces, upper surface is satiny and finely pubescent, lower surface is satiny and glabous, margins hairy.

Flower description:

*Inflorescence type*.—Compound terminal umbel.

*Lastingness of inflorescence*.—About 3 weeks from the opening of the first flower to senescence of last flower on inflorescence, individual flower lasts about 6 days, inflorescences are continuously produced during the bloom season.

*Inflorescence size*.—An average of 6 cm in height and 9 cm in width.

*Flower fragrance*.—Mild *pelargonium* fragrance.

*Flower number*.—Average of 23 per inflorescence.

*Flower aspect*.—Open flowers upright to outward with unopened flowers held downward.

*Flower bud*.—An average of 1.4 cm in length and 5 mm in width, narrow oblanceolate in shape, color; petal portion 44B, calyx portion 144C with shading of 152B, surface glabrous on petal portion and pubescent on calyx portion.

*Flower form*.—Rotate.

*Flower size*.—An average of 4 cm in diameter and 1 cm in depth.

*Petals*.—5, self-cleaning, both surfaces glabrous, rotate and non overlapping to slightly overlapping, obovate in shape, margins entire, apex rounded, base cuneate, an average of 2.2 cm in length and 2 cm in width, color when opening and fully open upper side; N30A with very base NN155B, color when opening and fully open lower side; 70N30B and very slightly flushed with 39B.

*Calyx*.—Campanulate in form, an average of 1 cm in length and 1.5 cm in width.

*Sepals*.—5, base lower 33% fused, lanceolate in shape, margins entire, apex acuminate, an average of 1 cm in length and 3 mm in width, upper surface is glabrous and satiny, lower surface pubescent, margins pubescent with long fine hairs, color; a bend of 144A and 144B on upper and lower surface.

*Peduncle*.—An average of 15 cm in length, 2 mm in width, N144D in color, held primarily upright, strong, surface pubescent.

*Pedicel*.—An average of 2.8 mm in length and 1 mm in width, N144D in color and slightly flushed with 184A, strong, held upright to outward, surface pubescent.

Reproductive organs:

*Gynoecium*.—Pistil; 1, stigmas; 5, 1 mm in length, and 60C in color, style; average of 2.5 mm in length and a blend of 60D and 145D in color, ovary 2 mm in length and 144A in color.

*Androcoecium*.—Stamens; Average of 10, anthers; oval in shape, 1 mm in length, 0.3 mm in width and 60A in color, filaments; 4 mm in length, lanceolate in shape, 60D in color on upper portion and NN155D on lower portion, pollen is moderate in quantity and 22A in color.

*Fruit/seeds*.—No fruit or seeds detected to date.

It is claimed:

1. A new and distinct cultivar of *Pelargonium* plant named 'Hughes Gold' as herein illustrated and described.

* * * * *